United States Patent
Shimoji

(10) Patent No.: US 6,325,791 B1
(45) Date of Patent: *Dec. 4, 2001

(54) METHOD OF USING A CORDLESS MEDICAL LASER TO CURE COMPOSITES

(76) Inventor: Yutaka Shimoji, 2125 University Ct., Clearwater, FL (US) 33764

( * ) Notice: Subject to any disclaimer, the term of this patent is extended or adjusted under 35 U.S.C. 154(b) by 0 days.

This patent is subject to a terminal disclaimer.

(21) Appl. No.: 09/375,062

(22) Filed: Aug. 16, 1999

Related U.S. Application Data

(63) Continuation-in-part of application No. 09/107,623, filed on Jun. 30, 1998, now Pat. No. 6,099,520, which is a continuation-in-part of application No. 08/872,085, filed on Jun. 10, 1997, now Pat. No. 5,928,220.

(51) Int. Cl.[7] .................................................. A61B 18/18
(52) U.S. Cl. ..................................... 606/2; 606/13; 606/17
(58) Field of Search ........................ 606/2, 9, 10, 13–17; 607/88–90, 92

(56) References Cited

U.S. PATENT DOCUMENTS

| | | | | |
|---|---|---|---|---|
| 5,233,283 | * | 8/1993 | Kennedy | 320/13 |
| 5,272,716 | * | 12/1993 | Soltz et al. | 372/109 |
| 5,616,141 | * | 4/1997 | Cipolla | 606/15 |
| 6,099,520 | * | 8/2000 | Shimoji | 606/2 |

* cited by examiner

*Primary Examiner*—Linda C. M. Dvorak
*Assistant Examiner*—P. J. Vrellakos

(57) ABSTRACT

A controlled process for thoroughly curing light-activated surgical and dental composites is presented using a hand-held, self-contained, cordless, rechargeable laser instrument. At least one diode laser generates focused laser light, and enhances efficiency and control of curing. The process of use includes switching from stand-by mode to curing mode of operation of the instrument to save time during surgical and dental procedures.

3 Claims, 1 Drawing Sheet

US 6,325,791 B1

METHOD OF USING A CORDLESS MEDICAL LASER TO CURE COMPOSITES

RELATED PATENT CROSS REFERENCE

This application is a continuation-in-part of U.S. patent application Ser. No. 09/107,623 filed on Jun. 30, 1998 now U.S. Pat. No. 6,099,520 which is a continuation-in-part of U.S. patent application Ser. No. 08/872,085, entitled "Cordless Dental and Surgical Laser", filed on Jun. 10, 1997 now U.S. Pat. No. 5,928,220.

BACKGROUND

The present invention relates to a method of using a medical laser instrument for curing dental and surgical composite materials, which provides single line laser light generation from a diode laser.

Cipolla discloses in U.S. Pat. No. 5,616,141 an argon laser dental instrument and method for curing dental composites. However, the laser light consists of multi-line bands of wavelength, of which some wavelength lines must be filtered, since they are not useful for the purpose of curing. Therefore, the system displays an inefficient way of producing the laser light necessary for the curing. In addition, the laser system is an argon gas laser for which a high power cooling system must be supplied in order to operate it. Furthermore, the argon gas laser requires high voltage and a high current power source. Therefore, the instrument can not be made into a compact, hand-held, self-contained unit. A large stationary unit is required to be connected to a separate hand-held portion by optic fibers and cables. Furthermore, the output of the argon laser consists of many lines of wavelength from blue to green of which only the blue line of 488 nm is useful for curing. The beam is collimated and, therefore, has constant power along the propagation length of the beam. This results in uncontrolled curing and air bubble entrapment due to the fact that the surface layers begin to cure prior to the deeper layers.

Paghdiwala discloses a focused pulsed Er:YAG laser for cutting in dental applications in U.S. Pat. No. 5,401,171. The laser light is generated within a hand-held tool, but the power supply and water cooling pump are external and not self-contained in a hand-held instrument and there is no method disclosed for curing composites.

Kowalyk et al. discloses a method for removing tooth decay in U.S. Pat. No. 5,456,603 using pulsed, frequency doubled lasers emitting red, green, deep blue, and UV light attenuated by some dye material. Consequently, none of wavelengths described match the maximum absorption wavelength of medical composites for curing. The device is not a compact, hand-held, self-contained instrument.

Therefore, there remains a need to provide an efficient method for laser curing of dental and surgical composite materials in a cordless, portable, self-contained, hand-held instrument which generates a single, optimum wavelength for each use.

SUMMARY

An object of the present invention is to provide a practical and efficient method for curing medical composites with laser light from a diode laser.

Another object of the invention is to provide a method of curing medical composite materials that overcomes the problems of incomplete and inefficient curing of the prior art.

These and other objects are achieved in the present inventive method of use of a cordless medical laser by generating and focusing a single line wavelength laser light from a hand-held, self-contained, diode laser instrument. Dental or surgical composites are cured by a focused wavelength of laser light matching the optimum absorption wavelength of the composite material used. The focal point is moved through the composite from the deep layers to the surface to ensure complete curing.

These and other objects and advantages of the present invention will become more apparent from the following drawing and description of preferred embodiment.

DESCRIPTION OF PREFERRED EMBODIMENT

Figure 1:
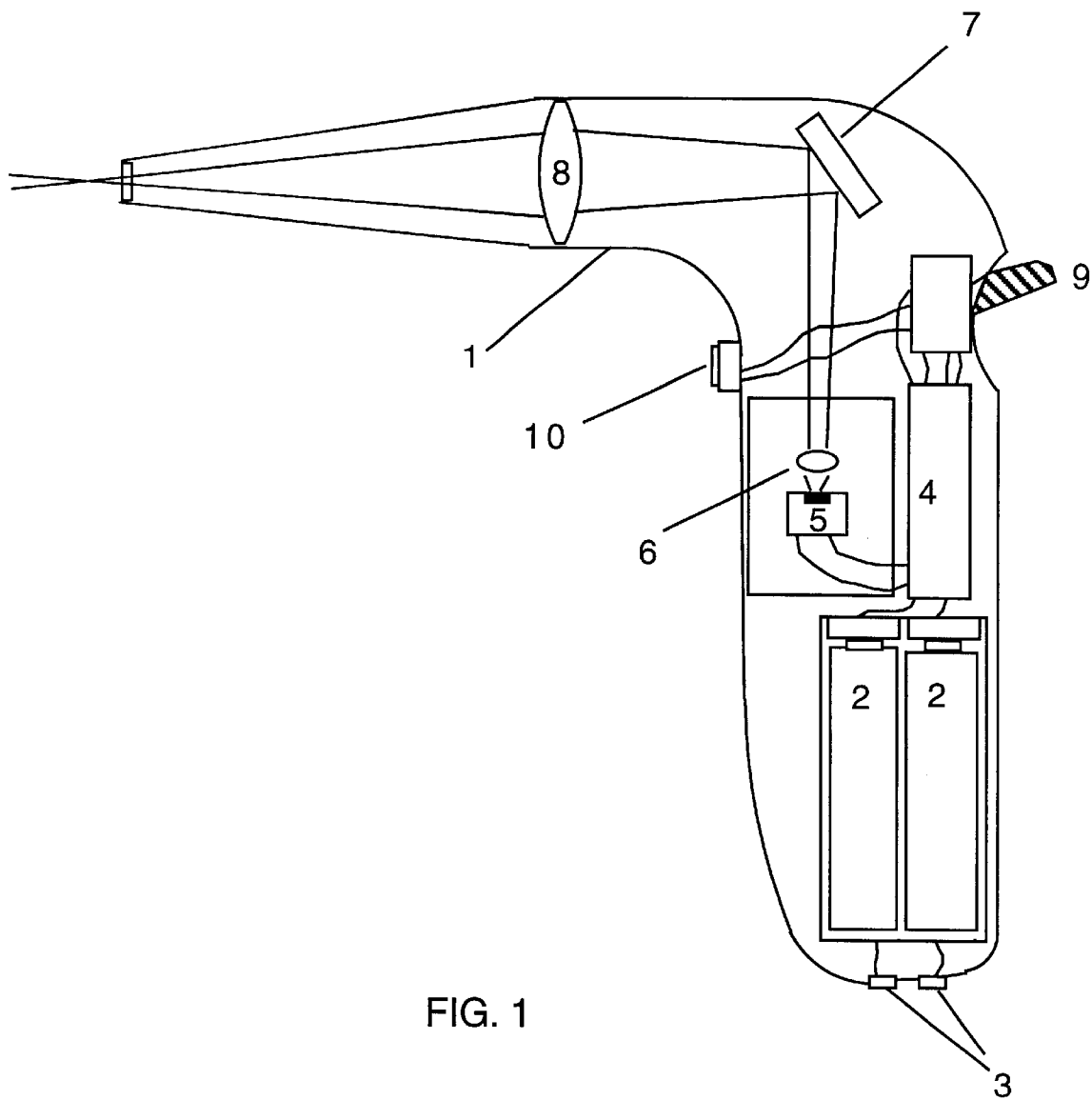
FIG. 1 is a longitudinal cross sectional view of the medical laser instrument used in the method of the present invention showing a diode laser for curing photopolymerizable materials.

The present invention is a method for curing surgical and dental composites using a hand-held, cordless, portable, self-contained diode laser instrument such as the one shown in FIG. 1. First a biological tissue site is exposed so that directed laser light can illuminate the site. The at least one diode 5 of the present invention includes, for example, InGaN as an active laser material. For the curing method of operation, a sufficient quantity of a chosen photopolymerizable medical composite material is placed at a site of repair and restoration. The instrument 1 is switched on by a stand-by switch 9, which turns on the electronics, so that the laser is ready to fire. The laser is fired by a firing switch 10. Both the firing switch 10 and the stand-by switch 9 are electrically connected to the laser driver electronics 4, which are electrically connected to the diode laser 5 and to the at least one rechargeable battery 2. The at least one battery 2 is electrically connected to the input electrodes 3. The output laser wavelength is selected to be the maximum absorption wavelength of the material to be cured. One example of the output laser wavelength is, optimally, 473 nm blue light, and at most 500 nm. The beam is focused through a lens 8 after being reflected from turning mirror 7. Laser light emitted from the at least one diode laser 5 is collimated through a microlens 6. The focused beam is directed into the chosen composite light activated material for a sufficient time for curing to occur. The output power is adjusted to the requirements of the targeted material by the diode laser driver electronics 4.

In another examlpe an optical fiber system is used to convey the laser light from the diode laser to the photopolymerizable material target, instead of the mirror 7, focusing lens 8, and microlens 6.

To enhance the completeness of curing, the focal point of the laser light is placed on the tissue/composite interface first, and then moved through the composite material to the surface, which is distal to the above interface. This eliminates air bubble entrapment and it enhances the bond between the composite material and the biological tissue to be repaired.

Since only one line of wavelength of laser light is generated by the at least one diode laser, no filters are needed and the power is used much more efficiently than in the prior art. So little power is required, that all of the components of the instrument 1 including the rechargeable batteries 2 with recharging electrodes 3, diode laser driver electronics 4, diode lasers 5, mirrors 7, and lens 8 are housed in a single unit hand-held, ergonomic, cordless, self-contained, portable, light-weight instrument housing, which has not been possible in the prior art. The at least one diode lasers are constructed out of any suitable lasing material not limited to InGaN.

A focused beam is superior to a collimated beam for curing due to the fact that light activation of deeper layers of photo-polymerizable medical composite material can be accomplished before the surface layer is cured.

The switch 9 ensures that the electronics are on and ready to fire at any time. Only one diode laser can be fired at a time. This saves a great deal of time in surgical and dental procedures, because the warm-up time prior to each firing is eliminated, and this reduces the possibility of infection far below that in the prior art.

Accordingly, for all these reasons set forth, it is seen that the method of the present invention represents a great advancement in the art of composite curing in surgery and dentistry, and has substantial commercial merit.

While there is shown and described herein certain specific process steps, structures, and methods, it will be manifest to those skilled in the art that modifications may be made without departing from the spirit and scope of the underlying inventive concept. The present invention shall not be limited to the particular process steps, structures, and methods herein described except by the scope of the appended claims.

What is claimed is:

1. A process of curing photo-polymerizable material comprising the steps of: placing quantity of a chosen photo-polymerizable material at a site of repair, said quantity being sufficient to effect repair; generating a laser light of a selected wavelength from inside a hand-held, self-contained, diode laser generation instrument containing at least one diode laser housed together with at least one rechargeable battery and a firing switch, said battery and said firing switch both being electrically connected to said diode laser, said firing switch being electrically connected to a stand-by-switch; directing said laser light from said instrument into said material for a sufficient time to effect curing of said material, a wavelength of said laser light being selected to be a maximum light absorption wavelength of said chosen material.

2. The process according to claim 1 wherein said laser light is collimated through a mirolens and focused through a focusing lens, said wavelength is at most 500 nm, and said diode laser includes InGaN as an active laser material.

3. The process according to claim 1 wherein the step of directing said laser light into said material is accomplished by first placing a focal point of said laser light at a biological tissue with said material, and then by moving said focal point from said biological tissue interface with said material in a direction toward a surface of said material, such that said material is cured at said biologically tissue interface initially and at said surface lastly.

* * * * *